| United States Patent [19] | [11] Patent Number: 4,801,886 |
|---|---|
| Steininger | [45] Date of Patent: Jan. 31, 1989 |

[54] MOUNTING MEANS FOR WATER CHEMISTRY ANALYSIS DEVICE

[76] Inventor: Jacques M. Steininger, 792 Hot Springs Rd., Santa Barbara, Calif. 93108

[21] Appl. No.: 44,440

[22] Filed: Apr. 30, 1987

Related U.S. Application Data

[63] Continuation-in-part of Ser. No. 864,477, May 19, 1986, Pat. No. 4,752,740.

[51] Int. Cl.[4] .................... G01N 27/56; F16L 5/02
[52] U.S. Cl. .................... 324/438; 255/197; 403/256
[58] Field of Search .............. 324/438, 439, 65 R, 324/446, 447, 448, 449; 210/96.1, 169; 403/240, 256; 285/197, 194, 206, 207

[56] References Cited

U.S. PATENT DOCUMENTS 3,825,483  7/1974  Nakamura .............. 324/438 X
3,941,665  3/1976  Eckfeldt et al. ............ 324/438
4,033,871  7/1977  Wall ...................... 210/96.1
4,091,324  5/1978  Diamond et al. ........... 324/449
4,329,650  5/1982  Teass, Jr. et al. ......... 324/449 X
4,502,011  2/1985  Druker ................... 324/446
4,507,521  3/1985  Goellner ................. 324/448
4,638,834  1/1987  Montgomery ............. 285/197 X

*Primary Examiner*—Reinhard J. Eisenzopf
*Assistant Examiner*—Robert W. Mueller
*Attorney, Agent, or Firm*—Marvin E. Jacobs

[57] ABSTRACT

An improved method of attachment of a pH or p sensor in the recirculation/filtration line for a pool or spa or for forming a T-connection between any two pipes comprises a saddle-clamp modified with an aperture to receive the shank of the sensor with an O-ring and a thinner, harder constricting ring surrounding the O-ring. When the saddle clamp is tightened, the constricting ring forces the O-ring toward the aperture while preventing excessive flattening of the O-ring.

13 Claims, 5 Drawing Sheets

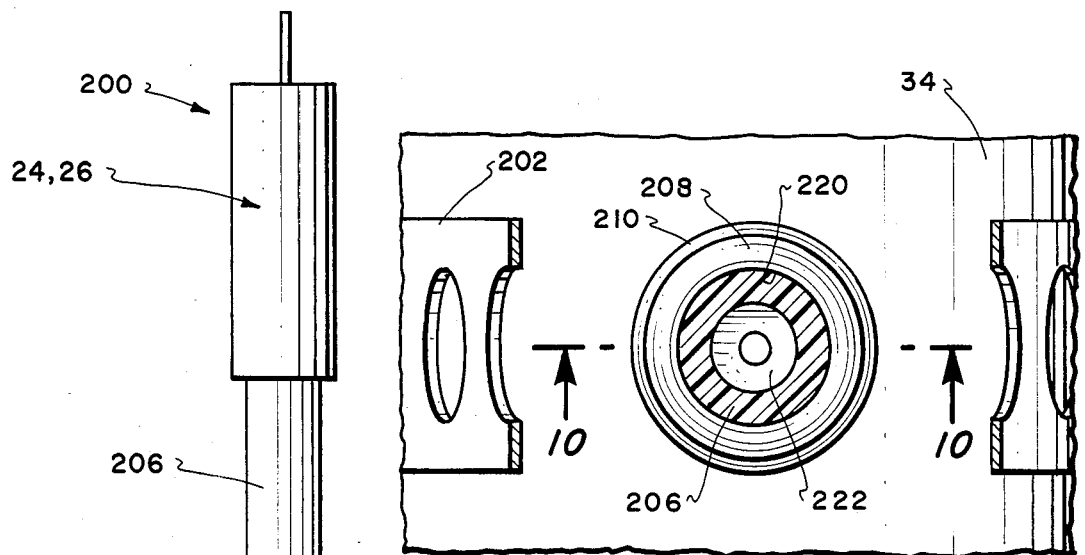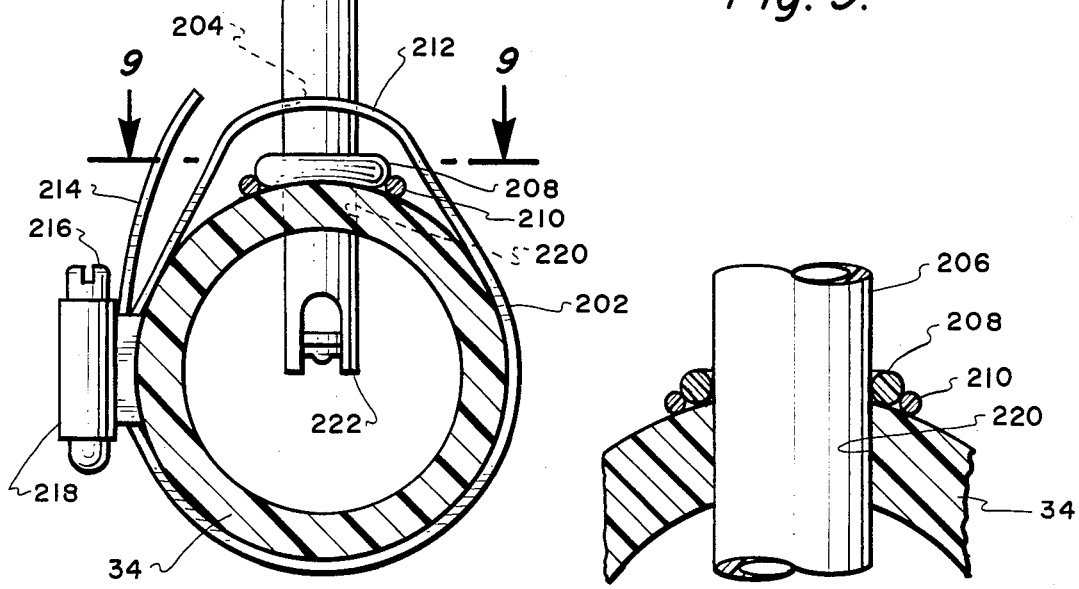

MOUNTING MEANS FOR WATER CHEMISTRY ANALYSIS DEVICE

CROSS-REFERENCE TO RELATED APPLICATION

The present application is a continuation-in-part of copending application Ser. No. 864,477 filed May 19, 1986, now U.S. Pat. No. 4,752,740.

TECHNICAL FIELD

The present invention relates to monitoring systems for the water of pools, spas, and the like and, more particularly, to a monitoring system having an oxidation-reduction potential (ORP) sensor means disposed in the water circulating system.

BACKGROUND ART

The growth in popularity of swimming pools, spas, and hot tubs has led to numerous sanitation problems caused by the difficulty of maintaining the proper chemical balance in the water. Improperly treated water leads to the proliferation of germs and bacteria. Similar sanitation problems also occur in other reservoirs of water, such as private or semi-public drinking water reservoirs, water supply tanks in recreational vehicles, cooling tower systems, etc.

Standard water sanitation methods are based on the use of chemical sanitizers, such as chlorine, bromine or ozone. In order to be effective, the sanitizers must be maintained constantly at well-defined concentration levels in the water, i.e., neither too high nor too low. This is often difficult to achieve in swimming pools and even more difficult in spas and hot tubs because of the high water temperature and the use of air jets, both of which tend to rapidly destroy or remove the sanitizer from the water. In addition, when several people get into these small bodies of water, they produce relatively large quantities of body wastes (sweat, etc.) which also deplete the sanitizer.

Pool or spa owners should, therefore, verify the chemistry of the water before anyone enters the water and even after a certain amount of time has been spent in the water. It is also necessary to add precise quantities of sanitizer as required to maintain the proper and safe concentration level thereof.

Up to now, the only practical way to verify the chemical balance in the water of most pools and spas has been with colorimetric chemical test kits using either liquid droplets, test strips or soluble tablets of a type such as that indicated generally as 10 in FIG. 1. In such a test kit, a test sample of water 12 from the pool or spa is scooped into bore 14. A staining agent 16 is then added as with the eyedropper 18. The degree of staining of the water 12 is determined, theoretically, by the amount of sanitizer in the water. This amount is then determined by comparing the degree of coloring of the water 12 against that of the preprinted test scale 20. Such test kits are inconvenient to use, complicated, and not very accurate. They can even give completely false readings in case of excess sanitizer due to bleaching of the staining solution. As a result, many people neglect the basic testing and chemical maintenance requirements and run the risk of becoming exposed to infections and diseases. These dangerous, unsanitary, and unhealthful conditions have been noted and reported by health departments all over the United States, Canada, and Europe, especially in commercial spas and hot tubs, bu also in many swimming pools.

Sophisticated electronic control systems that automatically monitor and maintain the chemistry of the water have been successfully manufactured and marketed for many years by several different companies; however, these devices are too expensive and too complicated for non-technical people and the average homeowner or small user. They also require a significant amount of maintenance, particularly for the chemical feeders. Consequently, they are used almost exclusively on large pools and spas, and not on the hundreds of thousands of smaller installations, commercial or residential, that need this type of protection just as much as the larger ones.

Recently, sanitarians at this year's National Environmental Health Association annual meeting were told that oxidation-reduction potential (ORP)—a mandatory standard for measuring water quality in West Germany's public pools and spas—ought to become a public health requirement in the United States.

Of related interest, a recently completed study of chemical and microbiological water-quality constituents for thirty public spas in the area of Portland, Oreg., found little correlation between the free-chlorine residual readings normally used to monitor them and the bacteriological quality of the spas themselves.

Normally, it is presumed that if you are maintaining a free-chlorine residual of two milligrams per liter or two parts per million (2 ppm), you have good water quality; but, the above-referenced test did not find this to be true. The only parameter that seemed to take into consideration all the constituents, including oil and grease concentration, was ORP. It was found that whenever the ORP residual was equal to or greater than 650 millivolts, the water was bacteriologically acceptable.

The National Sanitation Foundation (NSF) task committee that is currently reviewing pool and spa equipment standards, has pointed out that ORP is a well-known measurement in the field of sewage waste-water treatment. People who are knowledgeable in that area are frankly surprised that ORP is not being used for the monitoring and control of pools and spas. Public spas, in particular, are a prime target for ORP because organic loading makes potential disease transmission far more significant for public spas than for pools.

The above-referenced report suggests that bather loading, ORP, and chlorine effectiveness are directly related. The OTO chlorine test kit of FIG. 1 which is routinely sold in pool stores is unreliable because it fails to distinguish between free and combined chlorine. The parts-per-million reading determined from the stain comparison can actually be a reflection of combined chloramine, which does not protect bathers from bacteria and viruses.

Because organic and chemical loading significantly reduces the ability of free chlorine to overcome bacteria, DPD free chlorine test kits are also of questionable value unless the exact level of organic contaminant and the pH in the spa water can be determined.

West Germany's public health standards produce pool and spa water quality in that country which meets or exceeds Environmental Protection Agency drinking water standards in the United States. In West Germany, free chlorine levels of 0.2 to 0.4 ppm are considered more than adequate as long as the ORP is at an acceptable level of 650 millivolts or higher.

ORP is defined as the oxidation-reduction potential of a sanitizer such as chlorine, bromine or ozone. These oxidizers "burn off" impurities in the water, including body wastes, algae and bacteria. An ORP sensor measures the potential generated by the active form of the sanitizer, and not the inactive forms, such as combined chlorine. Unlike OTO or DPD "eyeball" testing as described above, ORP is an ongoing electronic process that requires no test chemicals or reagents and constantly monitors sanitation levels.

Persuading pool and spa industry people and public health officials to rely on ORP is a question of education and cost. NSF predicts the eventual adoption of an ORP standard for public and semi-public pool and spa facilities. Currently, a handful of manufacturers produce ORP probes, usually as a component of an automated chemical feeder system. Ironically, even managers of pools and spas who swear by chemical automation usually are unaware that ORP metering is built into these systems; the acronym is anything but a household word. ORP probes priced in the $80–100 range are now available and can monitor water on a continuous basis.

In some places, chemical automation is already mandatory. In Warren County, Ohio, for example, the General Health District requires installation of an electronic water-control device on all public spas and hot tubs to monitor and control free chlorine and pH. The same is true in Anchorage, Ak., where an automatic chlorinator with a sensor is required to insure proper levels of chlorine.

In a 1984 study in San Diego that included health club and condominium spas, out of fifty public spas surveyed, the researchers found that 24% of them were a source of parasitic infection and that more than 50% of them were under-chlorinated and had unhealthful bacteria. Thus, regardless of the costs, it is obvious that something must be done to guarantee the healthfulness of pools and spas on all levels.

STATEMENT OF THE INVENTION

The present invention provides a low cost system incorporating the ORP standard for monitoring pools, spas, and the like.

The inventive monitor for pools, spas, and the like, that can be used to handle complex electronic signals and convert them into simple readouts and operating instructions without costly and complicated electronic circuitry.

The monitoring system of the present invention for pools, spas, and the like includes a container filled with water for holding one or more bathers therein and a recirculating system for removing water from the container, filtering it, and returning it to the container. The monitoring system comprises, oxidation-reduction potential (ORP) sensor means disposed in the recirculating system for developing at an output thereof an electrical signal directly related to the active form of a sanitizer contained in the water; pH (PH) sensor means disposed in the recirculating system for developing at an output thereof an electrical signal directly related to the acidity/basicity level of the water; a first bargraph display; a second bargraph display; first electrical driver means operably connected between the output of the ORP sensor means and the first bargraph display for moving the first bargraph display in step increments between upper and lower limits corresponding to "more than necessary" and "less than necessary" levels of sanitizer in the water; second electrical driver means operably connected between the output of the PH sensor means and the second bargraph display for moving the second bargraph display in step increments between upper and lower limits corresponding to "lower acidity than optimum" and "higher acidity than optimum" levels of water; first scale means disposed adjacent the first bargraph display for indicating the millivolt signal from the output of the ORP sensor means and for indicating portions of the first bargraph display wherein sanitizer should be added to the water when the first bargraph display is indicating therein; and, second scale means disposed adjacent the second bargraph display for indicating the pH corresponding to the electrical signal from the output of the PH sensor means and for indicating portions of the second bargraph display wherein acid should be added to the water and base should be added to the water when the second bargraph display is indicating therein.

The present invention also relates to a simplified method for attachment of a sensor to the recirculating line. Attachment of sensors (usually ½ inch in diameter) on a pool or spa recirculation line (normally 1½ or 2 inches in diameter) by conventional methods constitutes a major plumbing problem involving cutting of the line, insertion and glueing or soldering of a reducing tee and insertion of a compression fitting. This work is too complicated for most homeowners and normally requires costly professional installation.

A simplified and inexpensive method of attachment of the sensor made possible by the invention permits free installation of the sensor by most homeowners, or at minimal cost by a professional installer.

The method of the invention only requires drilling of a ½-inch hole in the pipe and mounting of the sensor with a specially designed saddle clamp and O-ring assembly.

The seal is formed by an O-ring that fits tightly around the body of the sensor. A constricting ringlet around the O-ring prevents its expansion when it is compressed by the saddle clamp. Previous attempts to use an O-ring without the constricting ringlet resulted only in leaks and failure of the recirculation system. The present system is very effective and works practically every time, thus saving considerable time and money in installation.

Obviously, the present invention is also applicable to any size pipe or any diameter sensor. The attachment method is not limited to pools and spas. It is useful in joining any pipe to any other pipe carrying a liquid or gaseous fluid. The T-joint can be used to meter or inject one fluid into another fluid or simply to form a branch juncture. For example, the modified clamp of the invention could be used to tap an ice maker line into an existing water line.

These and many other features and attendant advantages of the invention will become apparent as the invention becomes better understood by reference to the following detailed description when considered in conjunction with the accompanying drawings.

DESCRIPTION OF THE DRAWINGS

FIG. 8 is a schematic view of an assembly for mounting in a sensor in a recirculating line;

FIG. 9 is a cross-section taken along line 9—9 of FIG. 8; and

FIG. 10 is a further view in section taken along line 10—10 of FIG. 9.

DESCRIPTION OF THE PREFERRED EMBODIMENT

The monitoring system of the present invention, to be described in detail hereinafter, uses the same type of electronic sensors that are used on the more expensive automatic controllers for pools or spas. These sensors are called ORP and pH electrodes and they can be purchased from many different manufacturers in the United States and overseas, such as the Broadley-James Corp. in Santa Ana, Calif. As less costly sensors become available, they can be substituted for the more costly sensors presently available to thereby provide the advantages of the present invention at an even lower cost. These sensors monitor the sanitizer and the pH level in the water and produce electronic signals that vary with the chemistry of the water. In the present invention, these signals are electronically converted by an amplification circuit and then displayed on linear bargraphs. Customized indicating scales are located next to the bargraphs. These scales are used to show the chemical concentration levels in simple non-technical terms and, additionally, to directly convey operating instructions for manual control of the water sanitizing and other conditioning chemicals in easy-to-understand language.

Figure 1:
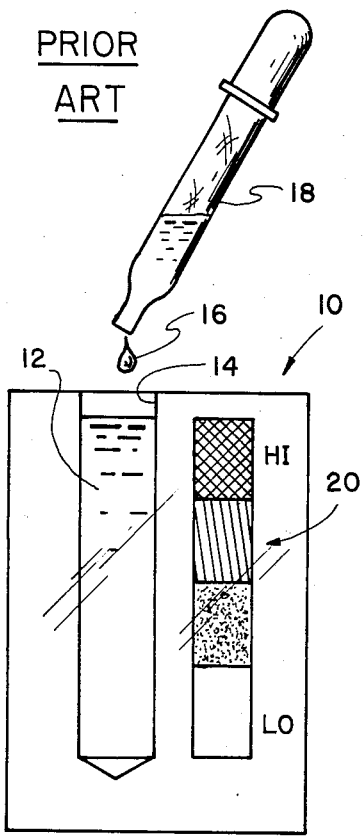
FIG. 1 is a simplified drawing of a prior art pool water test kit of the type wherein a visual determination of sanitizer level is made by comparison of staining level to a preprinted color scale.
Figure 2:
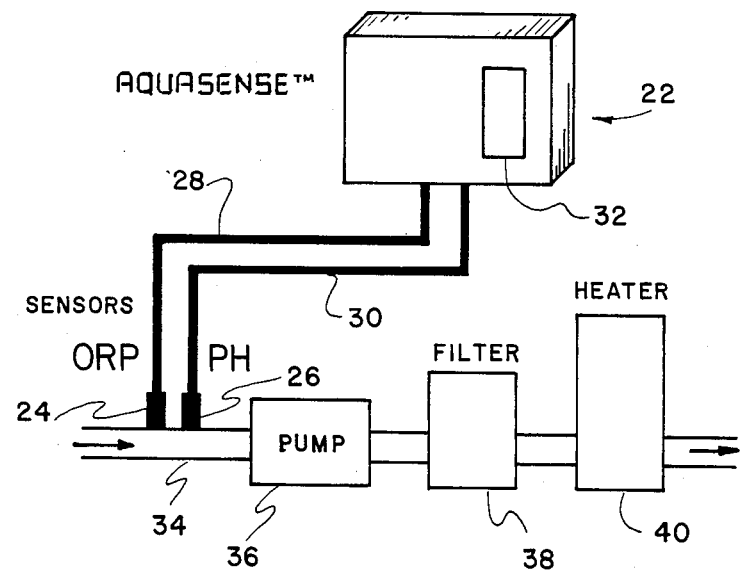
FIG. 2 is a simplified block diagram representation of the monitoring system of the present invention.

A preferred embodiment of the present invention as manufactured and sold commercially by applicant s company under the trademark AQUASENSE is shown and generally indicated as analyzer 22 in FIG. 2. As can be seen from the system diagram of FIG. 2, the ORP and pH sensors 24 and 26, respectively, continually sense the circulating water and are connected by wires 28 and 30, respectively, to the AQUASENSE analyzer 22, where a dual bargraph liquid crystal display 32, to be described in detail shortly, includes both a pH scale from 7.2 to 7.8 and an ORP scale showing millivolts (mV) of oxidation-reduction potential for the sanitizer from 500 mV to 900 mV. As should be readily recognized from the simplified drawing of FIG. 2, the monitoring system of the present invention has a major advantage over the prior art "eyeball" tests normally used with home spas and pools in that the water being sensed is not a fixed volume (which is normally dipped out of the pool at the top and near an edge and not necessarily representative of the majority of water volume), but rather, a constant monitoring of the water passing through the recirculation pipe 34 from the pool or spa leading into the pump 36, filter 38, heater 40, and back to the pool or spa.

As shown in FIGS. 8-10, the pH and water sensors 24, 26 are readily installed in the recirculation line 34 with the clamp assembly 200 of the invention. The assembly 200 includes a saddle clamp 202 having a circular aperture 204 with a diameter equal to the diameter of the shank 206 of the sensor 24, 26 and an O-ring 208 and a constricting ringlet 210. The clamp includes the conventional slotted belt 212 having one end 214 engaging a tightener bolt 216 carried in a sleeve 218. The O-ring 208 has an inner diameter such that it fits tightly onto the shank 206 of the sensor. The constricting ringlet 210 has an inner diameter just larger than the outer diameter of the O-ring 208 such that the O-ring 208 loosely fits within the ringlet. The ringlet 210 is formed of a much more rigid material than the elastomeric O-ring, suitably the ringlet is formed of an engineering plastic such as Nylon (a polyamide) The ringlet can have a circular or rectangular cross-section. A flat ringlet is readily fabricated by slicing a ringlet from a length of tubing. The ringlet must have a height less than the O-ring to allow compression of the O-ring to seal the sensor into the line. Suitably, the ringlet has a height from 40% to 60% of the diameter of the O-ring.

The sensors are installed by drilling two holes 220 in the recirculating line 34 having a diameter equal to the diameter of the shank of the sensors.

Before drilling the holes, make sure to stop the recirculation pump and drain the water if the pump is below the water line. Select a proper location for each sensor, i.e. before the pump, on top of the pipe and at least 3 inches apart. Using the ½-inch auger bit, drill two holes so that the sensors (with cap removed) can slide in easily. Do not overdrill the holes as this could result in air leaks and cause pump damage. Remove the protection caps at the tip of the sensors and store them in a safe place for winterizing or for possible reshipping of the sensors. Carefully insert each sensor 24, 26 through the aperture 204 in the steel clamp 202, one O-ring 208 and a constricting ringlet 210. Adjust this assembly on the sensor so that the tip 222 of the sensor will be positioned approximately in the middle of the pipe 34. Insert the sensor 24, 26 in the pipe and tighten up the clamp just enough to take up the slack of the strap. Overtightening may cause air leaks. Also make sure that the loose end of the strap does not cut into the sensor body. The pump is primed and run to check for leaks around the sensors. If there is a leak, tighten up the clamp screw one or two more turns or add some silicone sealant.

Figure 3:
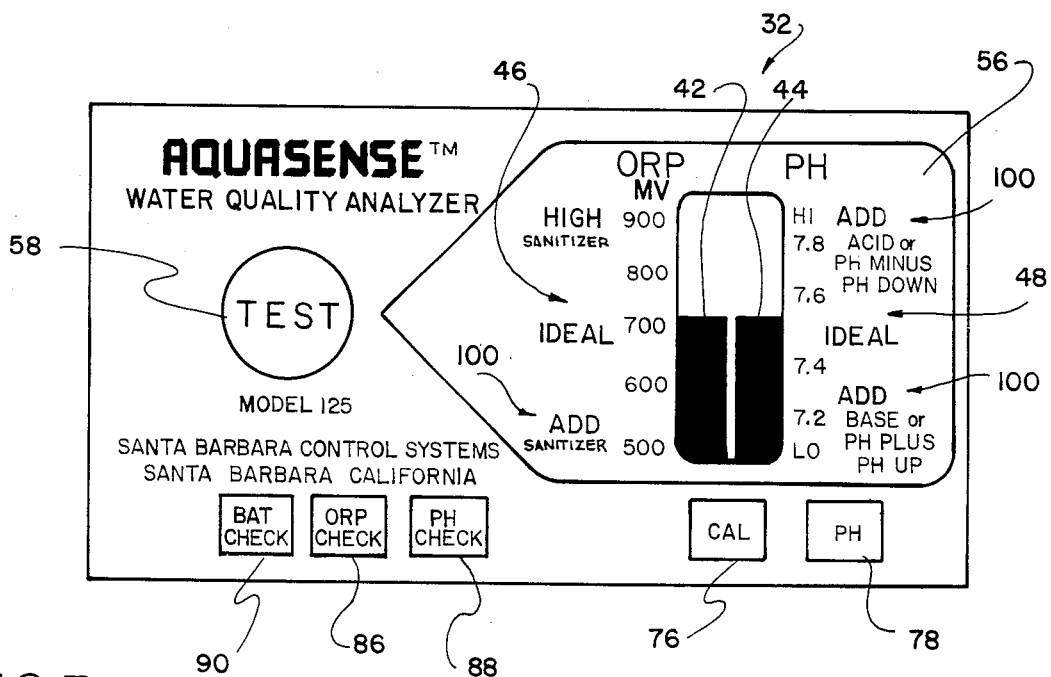
FIG. 3 is a detailed drawing of the display panel for the commercial embodiment of the monitoring device of the present invention with ORP millivolts and pH scales.

As mentioned earlier, ORP is directly related to the concentration and activity of the sanitizer in the water and has been recognized by international health authorities as a good indicator of water quality. In 1972, the World Health Organization recognized in their Standards for drinking Water that at an ORP level of 650 millivolts, the water is disinfected and viral inactivation is almost instantaneous. In the AQUASENSE analyzing system of the present invention, the ORP readings in millivolts are translated at the display 32 into simple instructions for the homeowner or serviceman to show whether the water is safe and whether chemicals need to be added. The display 32 of the present invention in its commercial embodiment is shown in greater detail in FIG. 3. Bar graph displays at 42 and 44 are used to display the ORP and pH readings, respectively. Scales 46 and 48 disposed adjacent to the displays 42, 44 provide the homeowner or service technician with a direct and easily understood indication of the ORP and pH levels, respectively, along with a direct indication of what action is to be taken, if any. The advantages of using an ORP scale at 46 instead of the more familiar parts-per-million (ppm) of free chlorine is that ORP is direct reading, does not need calibration, and applies to all sanitizers or combinations of sanitizers. In addition, it automatically reflects the effects of pH and other chemicals such as cyanuric acid stabilizer on the activity of the sanitizer.

Figure 4A:
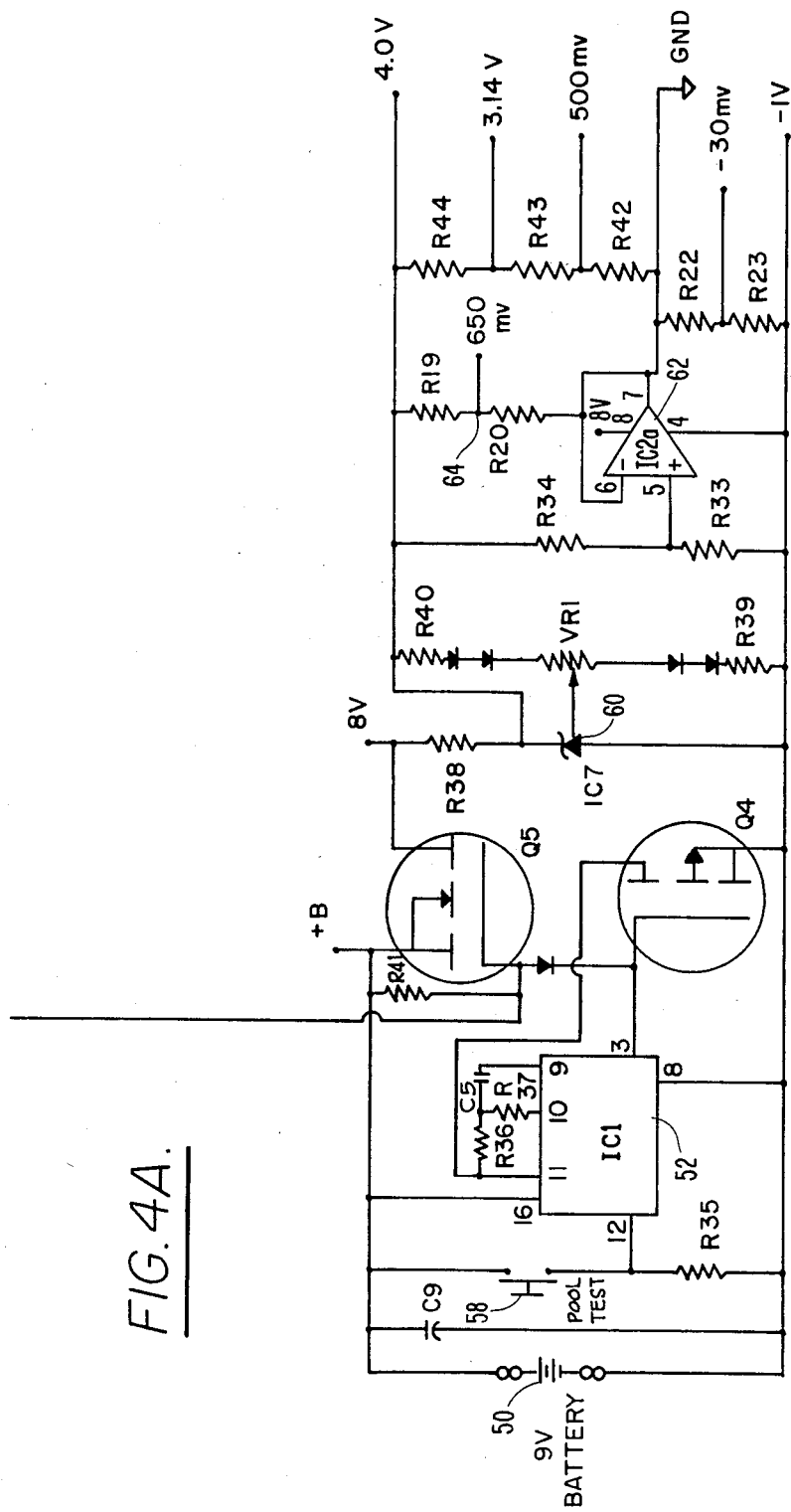
FIGS. 4A and 4B is the electronic circuit employed in the commercial embodiment of the present invention of FIG. 3.
Figure 4B:
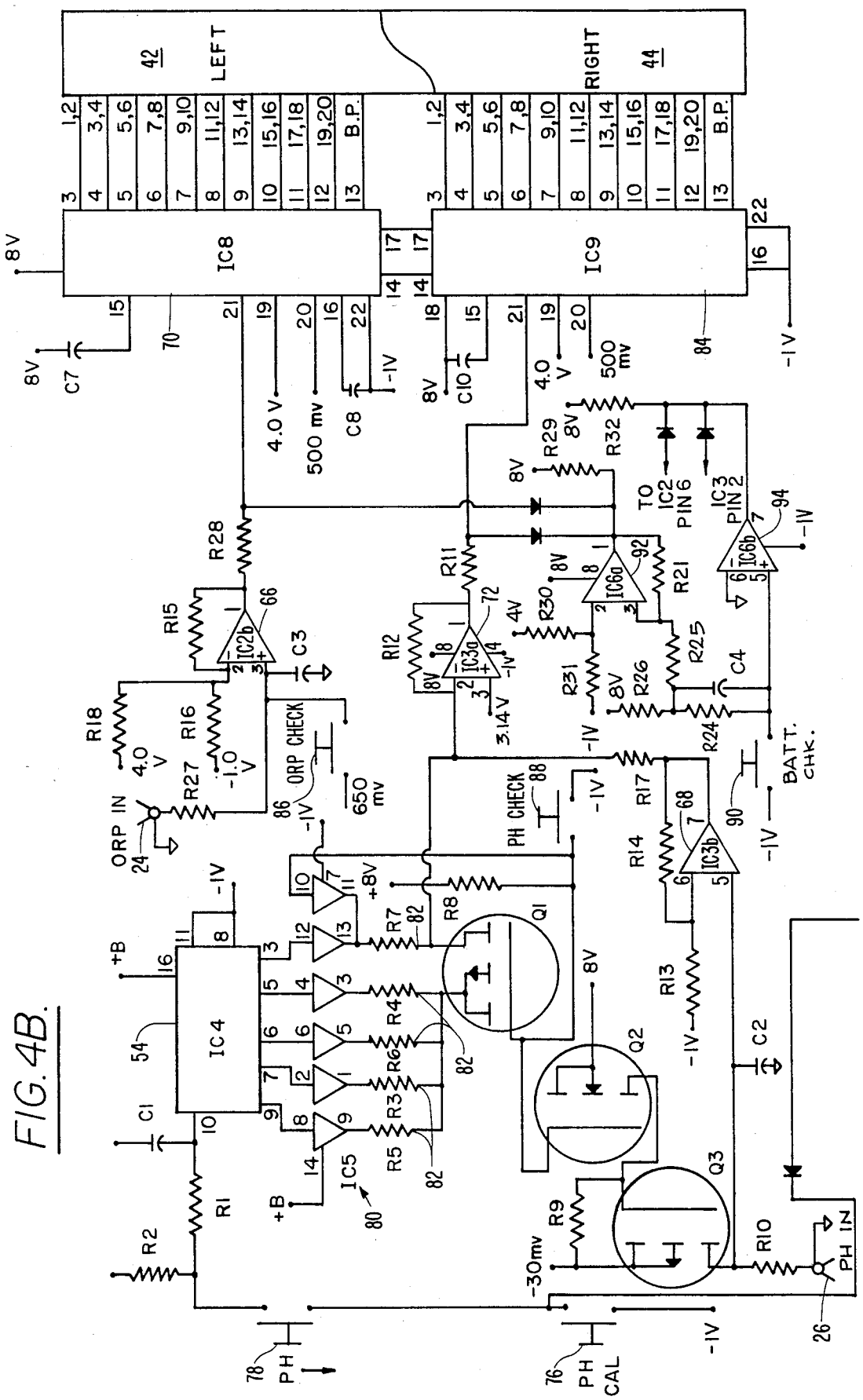

The electrical diagram for the AQUASENSE analyzer 22 in its commercial embodiment is shown in FIGS. 4A and 4B. The values of the components thereof are listed in Table I. For use around a pool/spa environment, the electrical switches and contacts to be described are of the so-called "membrane" variety and are disposed behind flexible portions of the panel 56 of the display 32 of FIG. 3. The operation of the circuitry of FIGS. 4A and 4B should be readily understood by those skilled in the art from an inspection thereof and, therefore, in the interest of simplicity of this application, the details thereof will be discussed broadly and not in minute detail.

TABLE I

| ITEM | VALUE | ITEM | VALUE |
| --- | --- | --- | --- |
| R1 | 1 M ohm | R2 | 100K ohm |
| R3 | 1.47 M ohm | R4 | 365K ohm |
| R5 | 2.98 M ohm | R6 | 732K ohm |
| R7 | 182K ohm | R8 | 100K ohm |
| R9 | 6.8 M ohm | R10 | 10 M ohm |
| R11 | 4.7K ohm | R12 | 205K ohm |
| R13 | 100K ohm | R14 | 383K ohm |
| R15 | 412K ohm | R16 | 118K ohm |
| R17 | 20.5K ohm | R18 | 301K ohm |
| R19 | 120K ohm | R20 | 25.5K ohm |
| R21 | 6.8 M ohm | R22 | 1.15K ohm |
| R23 | 37.4K ohm | R24 | 20K ohm |
| R25 | 100K ohm | R26 | 130K ohm |
| R27 | 10 M ohm | R28 | 4.7K ohm |
| R29 | 100K ohm | R30 | 200K ohm |
| R31 | 49.9K ohm | R32 | 100K ohm |
| R33 | 11.3K ohm | R34 | 45.3K ohm |
| R35 | 2 M ohm | R36 | 2 M ohm |
| R37 | 6.8 M ohm | R38 | 1.8K ohm |
| R39 | 4.99K ohm | R40 | 4.99K ohm |
| R41 | 100K ohm | R42 | 4.99K ohm |
| R43 | 25.5K ohm | R44 | 8.66K ohm |
| VR1 | 2K ohm | C1 | 47 Nfd |
| C2 | 10 Nfd | C3 | 10 Nfd |
| C4 | 10 ufd | C5 | 1 Nfd |
| C6 | (unused) | C7 | 4.7 ufd, 16 V |
| C8 | 3.9 ufd, 16 V | C9 | 47 ufd, 16 V |
| C10 | 4.7 ufd, 16 V | IC1 | 4060 |
| IC2 | 3240A | IC3 | 3240A |
| IC4 | MCI 4040 | IC5 | 74C906 |
| IC6 | 393 | IC7 | LM336Z-5.0 |
| IC8 | IR 2429 | IC9 | IR 2429 |
| Q1, Q3, Q4 | VN2222L | Q2, Q5 | VP0300L |
| All Diodes | 1N914 | | |

Where:
ufd = microfarad = 1 × 10$^{-6}$ farad
Nfd = Nanofarad = 1 × 10$^{-9}$ farad The voltage of the 9 volt battery 50 is continuously applied to integrated circuits IC1 and IC4 (52 and 54, respectively) so that the run timer IC1 is standby powered and the pH probe calibrate counter/memory retains its current value.

When the [TEST] contact pad 58 is pressed, IC1 (52), an oscillator/counter, is initialized to zero, turning on the powersupply to +8 volts. Releasing the [TEST] pad 58 allows IC1 (52) to oscillate and count. After approximately 30 seconds, IC1 (52) will shut off the +8 volts and prevent itself from oscillating until once again it is reset by pressing the [TEST] pad 58. The object of the timing and automatic shutoff is to conserve battery power and increase its longevity between replacements. This part of the circuit can be eliminated or bypassed if the unit is connected to a constant power supply instead of an expendable battery as shown.

When the +8 volts is on, IC7 (60) sets 5.00 volts difference between the 4.0 and the −1.0 regulated voltages. IC2a (62) provides a low impedance source for zero volts (circuit reference or "ground"). Other bias and test voltages are derived from the resistor dividers at 64.

The electronic signals from the two sensors 24, 26 at ORP IN and PH IN, respectively, are filtered then buffered by the non-inverting amplifiers IC2b and IC3b (66, 68), respectively.

On the ORP side, feedback and bias resistors cause the ORP signal to be conditioned to the proper range for displaying on the left side bargraph 42 of the liquid crystal display, which is 500 to 900 millivolts full scale. IC8 (70) converts the input DC voltage level to the format of the liquid crystal display bargraph 42.

On the pH side, the output of the pH amplifier is one input to a summing junction. The other input to this junction is the pH probe calibration offset current. This current and the pH buffer/amplifier signal are conditioned by IC3a (72) to be in the proper range for displaying on the bargraph 44 on the right side of the liquid crystal display, in this case 0 to −50 millivolts. IC4 (74) is a binary up-counter. It is incremented when the two contact pads 76 and 78, marked [CAL] and [PH], respectively, are pressed simultaneously. As this counter increments, IC5 (80) switches the five resistors 82 between −1.0 volt and an open circuit. Since the resistors 82 are normally connected to the aforementioned summing junction, the voltage to be displayed can be raised incrementally. The values of the resistors are chosen to produce increments of 10% on the display. IC9 (84) converts the input DC voltage levels to the format of the liquid crystal display bargraph 44.

When the [ORP CHECK] contact pad (86) is pressed, a fixed voltage forces the probe buffer input to a predetermined value of 650 millivolts so that the buffer and display circuits operation can be checked.

When the [PH CHECK] contact pad 88 is pressed, a fixed voltage forces the probe buffer input to a predetermined value of −30 millivolts. To assure the predetermined value, the pH probe offset is also forced temporarily to its center value.

When the [BAT CHECK] contact pad 90 is pressed, both ORP and pH voltages at the display section inputs are initially clamped to a low value (off scale downward) by IC6a (92). At the same time, both ORP and pH voltages to the display 32 are forced to maximum by IC6b (94). Two series resistors prevent excess current from flowing. If the battery voltage is high enough, the downscale clamp is released after a short delay and the display section now receives full upscale voltage. The result is an initial blank display then full scale display if the battery is good.

Figure 5:
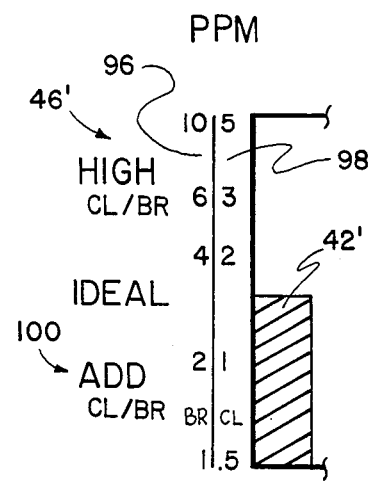
FIG. 5 is a display panel for the monitoring device of the present invention in an alternate embodiment having ppm free chlorine and pH scales.

In another possible embodiment of the present invention, the scale corresponding to the electronic signal from the oxidation-reduction potential (ORP) electrode 24 is labeled in parts-per-million (ppm) of free chlorine as shown in FIG. 5. The electronic signal (in millivolts) generated by the ORP electrode 24 varies in a complex manner with the concentration (ppm) and chemical form of the sanitizer in the water. It also varies with the pH of the water and with the concentration of other chemicals that may be present in the water; for instance, cyanuric acid, a stabilizer that is commonly used to protect chlorine from decomposition by the ultraviolet rays of the sun.

Figure 6:
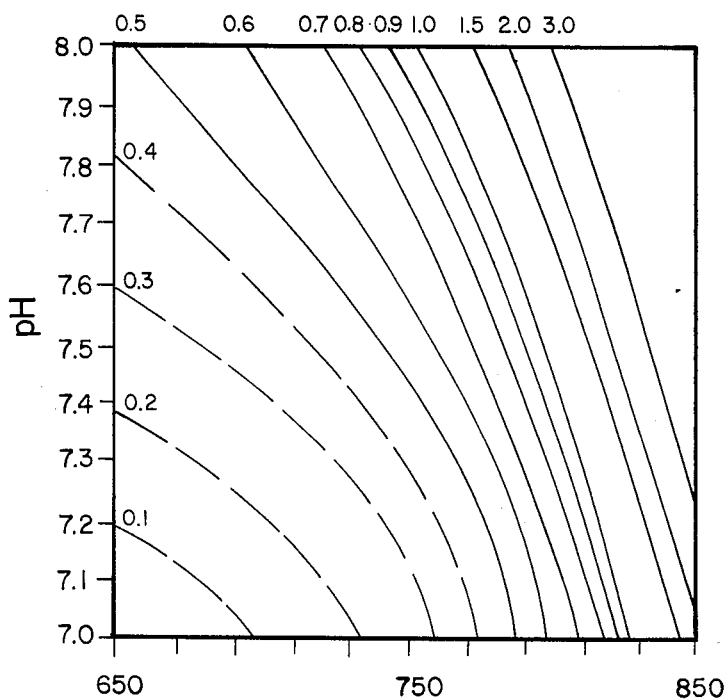
FIG. 6 is a graph of curves showing the relationship between ppm of free chlorine and ORP millivolt readings as a function of pH in the absence of cyanuric stabilizer as used to prepare the scales used in conjunction with the linear bargraph displays of the present invention.

The set of curves shown on FIG. 6 give a representation of the sensor signal as a function of chlorine concentration and pH level. One can see that each curve varies non-linearly in a very complex manner and that a whole set of curves is required to represent the effect of variations in pH level. In addition, these curves are valid only when there is no cyanuric stabilizer in the water. If there is a cyanuric stabilizer in the water, one needs a complete set of curves for each different concentration level of stabilizer. To date, nobody has even attempted to determine these curves. In other words, the complexity of the relationship between the electronic signal of the sensor and the chemical conditions in the water is impossible to represent mathematically and would be very difficult and expensive to reproduce electronically. This is one of the reasons why there is no electronic monitoring device of this type on the market today.

In the embodiment of FIG. 5, the linear bargraph display 42' for the sanitizer is used to show the variations of the sensor signal. Instead of converting the signal electronically however, the conversion is made graphically with a non-linear scale 46' which is placed adjacent the bargraph display 42'. The scale 46' is determined from curves such as those on FIG. 6. The user needs only to calibrate the unit and then read the variations in sanitizer and pH levels on the scales. The preferred method for calibration of the pH scale is to place the pH sensor in water of known pH value, preferably a buffer solution of fixed pH value. If no such solution is available, the water of the pool or spa can be used after its pH value is determined with a reliable pH test kit, such as a Phenol Red solution.

One additional advantage of linear bargraph displays as employed in the present invention is that they look very similar to the colorimetric scales that are used with chemical test kits. Most pool or spa owners are familiar with these scales and it is therefore easy for them to interpret the linear bargraph scales.

Figure 7:
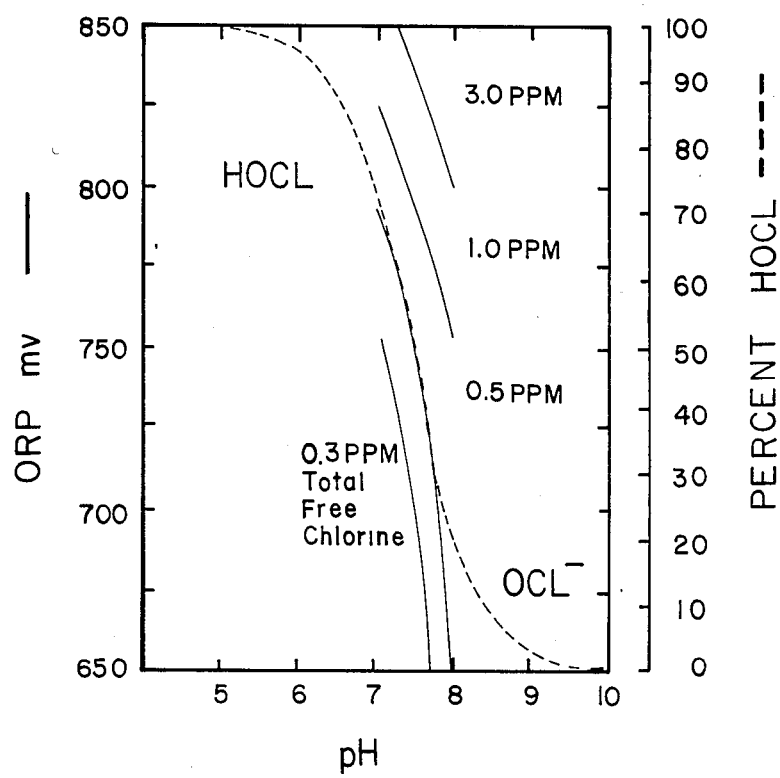
FIG. 7 is a graph of curves showing ORP millivolts v. pH for the active form of free chlorine as would be used in preparing the dual scale shown in the embodiment of FIG. 5.

As also shown on FIG. 5, the same bargraph display 42' can also be used for two different chemicals with different rates of variation represented by different scales incorporated as part of the scale 46'. In this instance, the bargraph display 42' on the left side is used with two separate scales, one for chlorine (96) reading from 0.5 to 5 ppm (parts-per-million or milligrams per liter) and one for bromine (98) reading from 1 to 10 ppm. Note that both sanitizer scales 96, 98 are very precisely calculated form curves such as those shown in FIG. 7. They are non-linear, i.e., the distance between 1 and 2 ppm (parts-per-million) is greater than the distance between 3 and 4 and even still greater than the distance between 8 and 10.

As one important aspect of the present invention, it should be noted that simple instructions, as at 100, have also been added to the scales 42' to advise the user either that the concentration level is appropriate or that corrective action should be taken and what that corrective action should be. The specific nature of the correction is indicted directly on the scale; such as "add acid", "add base", "add chlorine", etc. Years of experience in the pool and spa industry have shown that non-technical people are easily confused and afraid to use chemical concepts such as pH values or ppm levels using numbers shown on meters or digital readouts. The present invention eliminates this problem by providing simple instructions in everyday language. If desired, of course, it can also be used to show common chemical names or trade names of specialty chemicals. The fact that the AQUASENSE analyzer of the present invention described herein shows the user how to correct for improper water chemistry but does not actually feed the chemicals is important because it eliminates the problems caused by chemical feeders. Therefore, this makes it practically maintenance-free, the only maintenance required being the cleaning of the sensors if they become dirty. This also results in very low power consumption, which means that the device can be operated for a year or more on small battery power and does not require any electrical wiring.

While the analyzing system of the present invention is intended primarily for use by homeowners and small commercial users, it can also be used conveniently by pool and spa servicemen for quickly and accurately testing of water quality. By eliminating the need for calibration, the unit can be made portable and the ORP reading can be used on different pools and spas to determine the quality of the water. If the ORP reading is above a certain level, say 650 millivolts, the serviceman knows that the water meets the standards for drinking water. If it is below that level, he knows that he must add more sanitizer or check the pH and cyanuric acid levels.

The bargraph display described above which is incorporated into the present invention is a high-technology electronic device which can be made easily with a liquid crystal display or a set of light emitting diodes. For battery operation as shown in the example described herein, liquid crystal displays are preferred since they have much less current drain when used with battery operation.

Thus it can be seen that the present invention provides a new and novel water analysis system for use with pools, spas, and the like, which provides much more accurate information, ease of operation, and direct instructions on corrective action to be taken, if any, than available with analysis systems according to the prior art.

It is to be realized that only preferred embodiments of the invention have been described and that numerous substitutions, modifications and alterations are permissible without departing from the spirit and scope of the invention as defined in the following claims.

I claim:

1. A water analysis system for continuously analyzing the water in a recirculating line for pool, spa or the like, comprising in combination:

a set of adjacent sensors for mounting in said line said sensors including:

a cylindrical shaft surrounding each of said sensors;

a first oxidation-reduction potential (ORP) sensor mounted on the wall of the line with a sensing probe dispersed in the water in the line for developing a first electrical signal at its output directly related to the active concentration of the form of an oxidation sanitizer contained in the water;

a second pH sensor mounted on the wall of the line with a sensing probe dispersed in the water in the line for developing a second electrical signal at its output directly related to the acidity/basicity level of the water in the line;

means for mounting each of the probes on the wall of the line including an aperture through said wall for receiving the shaft, an assembly of an inner O-ring and an outer constricting ring slidably mounted on the shaft, said constricting ring being harder than the O-ring and having a height smaller than the diameter of the O-ring slidingly positioned on the outside edge of the O-ring and a belt clamp having an aperture receiving the shaft of the sensor and having a belt surrounding the line and means for tightening the belt clamp whereby the clamp flattens the O-ring between the belt and the wall of the line while it is constrained by the outer constraining ring;

an analyzer unit having a housing covered by a face plate and including:

a first bargraph display having a visual indicator movable over a first range corresponding to concentrations of sanitizer below and above optimum concentration mounted on said face plate;

a first sanitizer scale having a height equal to said first range printed on the face plate adjacent the first bargraph display indicating in the below optimum portion of the range a printed instruction to add sanitizer;

a second bargraph display having a visual indicator movable over a second range corresponding to pH mounted on said face plate;

a second scale printed on the face plate adjacent the second bargraph having a height equal to the second range including printed instruction in the high pH range to add acid and a printed instruction in the low pH range to add base;

a compartment within said housing for receiving a battery;

first electrical driver means electrically connected to said battery compartment and operably connected between the output of said first sensor and the first bargraph display for moving the first bargraph display in step increments over the first range; and second electrical driver means electrically connected to said battery compartment and operably connected between the output of the second sensor and the second bargraph display moving the second bargraph display in step increments over the second range.

2. The improvement to a water analysis system of claim 1 wherein:
(a) said first electrical driver means is adapted to drive said first bargraph display between upper and lower limits of 900 mV and 500 mV; and,
(b) said second electrical driver means is adapted to drive said second bargraph display between upper and lower limits corresponding to pH values of 7.8 and 7.2.

3. The improvement to a water analysis system of claim 2 wherein:
said first scale means disposed adjacent said first bargraph display for indicating the millivolt signal from the output of the ORP sensor includes indicia calibrating said first scale to indicate parts-per-million of free chlorine.

4. The improvement to a water analysis system of claim 3 wherein:
said first scale means disposed adjacent said first bargraph display for indicating the millivolt signal from the output of the ORP sensor includes indicia calibrating said first scale to indicate the presence of two different sanitizers.

5. The improvement to a water analysis system of claim 4 wherein:
said first scale means includes first indicia reading from 0.5 to 5 parts per million for indicating the presence of chlorine and second indicia reading from 1 to 10 parts per million for indicating the presence of bromine.

6. In a pool or a spa having a line for recirculating a water stream in which a chemical sensor having a tubular shaft, carrying a sensing element is received, the improvement comprises:
means for sealingly mounting the sensor in an aperture in the line with the sensing element disposed in the water stream in the line;
an assembly of an outer constricting ring and an inner O-ring with the O-ring slidingly mounted on the shaft;
said constricting ring having a greater hardness than the O-ring and a smaller thickness than the O-ring;
a cylindrical belt clamp surrounding the line having an aperture for receiving the shaft with the assembly of the O-ring and constriction ring disposed below the surface of the belt; and
means attached to the clamp for tightening the belt whereby a compression force is applied to the O-ring which flattens the O-ring between the outer surface of the line and the inner surface of the belt as constricted by the outer ring and seals the shaft in the aperture in the line.

7. The sensor mounting means of claim 6 in which the O-ring is an elastomer and the constricting ring is a rigid, engineering plastic.

8. The sensor mounting means of claim 6 in which the constricting ring has a height smaller than the diameter of the O-ring.

9. The sensor mounting means of claim 8 in which the constricting ring is formed of Nylon.

10. A coupler for forming a T-connection between a first pipe and a second pipe, said first pipe having an aperture for tightly receiving the second pipe;
an assembly of compressible O-ring and an outer adjacent constricting ring received on the second pipe;
said compressible O-ring having an inner diameter substantially equal to the outer diameter of the second pipe;
said constricting ring being formed of a harder, less compressible material than the O-ring; having an inner diameter substantially equal to the outer diameter and having a height less than the diameter of the O-ring;
a flat ring clamp having an opening for receiving the second pipe encircling the first pipe with said assembly being positioned between the lower surface of the ring clamp and the outer surface of the first pipe; and
means for tightening the clamp around the first pipe whereby said O-ring is compressed to seal the aperture in the first pipe.

11. A coupler according to claim 10 in which the tightening means comprises a series of axial slots on the ring clamp and a threaded bolt mounted advance the clamp past the bolt on rotation of the bolt to reduce the circumference of the clamp.

12. A coupler according to claim 10 in which the first pipe is formed of a synthetic resin.

13. A coupler according to claim 12 in which the first pipe is formed of polyvinyl chloride.

* * * * *